US012765806B2

(12) United States Patent
Fregly

(10) Patent No.: US 12,765,806 B2
(45) Date of Patent: Oct. 20, 2026

(54) MULTIBODY MOTION TRACKING USING MACHINE LEARNING-INFORMED PHYSICS MODELS AND INERTIAL MEASUREMENT UNITS

(71) Applicant: William Marsh Rice University, Houston, TX (US)

(72) Inventor: Benjamin J. Fregly, Houston, TX (US)

(73) Assignee: William Marsh Rice University, Houston, TX (US)

( * ) Notice: Subject to any disclaimer, the term of this patent is extended or adjusted under 35 U.S.C. 154(b) by 144 days.

(21) Appl. No.: 18/866,465

(22) PCT Filed: May 19, 2023

(86) PCT No.: PCT/US2023/022941
§ 371 (c)(1),
(2) Date: Nov. 15, 2024

(87) PCT Pub. No.: WO2023/225323
PCT Pub. Date: Nov. 23, 2023

(65) Prior Publication Data

US 2025/0331737 A1 Oct. 30, 2025

Related U.S. Application Data

(60) Provisional application No. 63/365,000, filed on May 19, 2022.

(51) Int. Cl.
*A61B 5/11* (2006.01)
*A61B 5/00* (2006.01)

(52) U.S. Cl.
CPC ........... *A61B 5/1122* (2013.01); *A61B 5/1114* (2013.01); *A61B 5/4528* (2013.01); *A61B 2562/0219* (2013.01)

(58) Field of Classification Search
CPC ... A61B 5/1122; A61B 5/1114; A61B 5/4528; A61B 2562/0219; A61B 5/112; A61B 5/1121; A61B 5/7267; G01C 25/005
See application file for complete search history.

(56) References Cited

U.S. PATENT DOCUMENTS 11,803,241 B2 * 10/2023 Cotton ................ A61B 5/0022
2017/0103541 A1 4/2017 Bellusci et al.

FOREIGN PATENT DOCUMENTS

EP 3552538 B1 9/2021

OTHER PUBLICATIONS

International Search Report issued in corresponding International Patent Application No. PCT/US2023/022941, mailed on Sep. 11, 2023 (4 pages).

(Continued)

*Primary Examiner* — Joel Lamprecht
(74) *Attorney, Agent, or Firm* — Osha Bergman Watanabe & Burton LLP

(57) ABSTRACT

A computer-implemented method for calculating multibody motion data includes obtaining measured IMU data time histories with a plurality of inertial measurement units and using computer-based algorithm incorporating a machine-learning informed kinetic model to generate the multibody motion data. A system for generating motion data from a multibody system includes include a plurality of inertial measurement units, each configured to be placeable on a corresponding segment of the multibody system and a computer system comprising a processor configured to implement the computer-based algorithm.

16 Claims, 14 Drawing Sheets

(56) References Cited

OTHER PUBLICATIONS

Written Opinion issued in corresponding International Patent Application No. PCT/US2023/022941, mailed on Sep. 11, 2023 (6 pages).
Li Tong et al, "Reconstructing Walking Dynamics From Two Shank-Mounted Inertial Measurement Units", Jan. 14, 2021, vol. 26, No. 6, p. 3040-3050 (11 pages).
Palomba Ilaria et al, "Kinematic state estimation for rigid-link multibody systems by means of nonlinear constraint equations", Mar. 23, 2016, vol. 40, No. 1, p. 1-22 (22 pages).

* cited by examiner

MULTIBODY MOTION TRACKING USING MACHINE LEARNING-INFORMED PHYSICS MODELS AND INERTIAL MEASUREMENT UNITS

CROSS-REFERENCE TO RELATED APPLICATIONS

This application claims benefit of U.S. Provisional Patent Application Ser. No. 63/365,000, filed May 19, 2022, which is herein incorporated by reference.

STATEMENT REGARDING FEDERALLY SPONSORED RESEARCH

This invention was made with government support under Grant No. 1805896 awarded by the National Science Foundation. The government has certain rights in this invention.

BACKGROUND

There is interest in measuring the motion of systems of interconnected rigid bodies, where the bodies are considered to be connected by traditional engineering constraint-based joints (e.g., pin joints, ball-and-socket joints). Such systems include the human body, industrial robots, rehabilitation robots, and industrial cranes to name a few. Motion measurement of such systems is traditionally performed using marker-based video motion capture technology, which places active or passive markers on the system's rigid bodies and measures system motion in a small, controlled, and calibrated test environment, typically indoors (though some systems now work outdoors as well).

While numerous inertial measurement unit (IMU)-based motion measurement systems already exist (including a number of commercial options), existing systems are complicated to use, tend to require knowledge of initial conditions for IMU orientations, positions, and velocities along with kinematic model joint positions and velocities, and tend to require that one IMU be attached to each body segment (i.e., a full set of IMUs). Furthermore, most IMU-based motion measurement methods use some type of filtering algorithm (e.g., Kalman filter, extended Kalman filter, unscented filter) to convert IMU measurements of linear acceleration (including the acceleration due to gravity, which must be eliminated) and angular velocity into estimates of body or joint positions and orientations. Commercial systems currently tend not to work with a minimal set of IMUs. A minimal set of IMUs would make the system much easier to use by untrained individuals (e.g., patients receiving remote physical rehabilitation) in any environment. Therefore, there exists a need for improved methods, which are simple and cost efficient, to calculate the motion of a multibody system.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a computer-implemented method for calculating multibody motion data. The method may include obtaining measured IMU data time histories with a plurality of inertial measurement units. The method may include inputting the measured IMU data time histories and a guess for a plurality of joint position design variables into an analytical function to calculate joint position, velocity, and acceleration time histories. The method may include inputting the calculated joint position, velocity, and acceleration time histories into a kinematic model to calculate kinematic model predictions of IMU angular velocities and gravity-corrupted linear accelerations. The method may include inputting the measured IMU data time histories into a machine learning model to calculate machine learning model predictions of joint positions, velocities, and accelerations. The method may include determining optimal values for the plurality of joint position design variables by optimizing the guess for the plurality of joint position design variables using a cost function, where the cost function includes a first type of error associated with matching IMU angular velocities and gravity-corrupted linear accelerations and a second type of error associated with matching joint positions, velocities, and accelerations generating the multibody motion data using the optimal values for the plurality of joint position design variables. The method may include generating the multibody motion data using the optimal values for the plurality of joint position design variables.

In another aspect, embodiments herein disclosed relate to a system for generating motion data from a multibody system. The system may include a plurality of inertial measurement units, each configured to be placeable on a corresponding segment of the multibody system. The system may include a computer system comprising a processor configured to input the measured IMU data time histories and a guess for a plurality of joint position design variables into an analytical function to calculate joint position, velocity, and acceleration time histories. The processor may be configured to input the calculated joint position, velocity, and acceleration time histories into a kinematic model to calculate kinematic model predictions of IMU angular velocities and gravity-corrupted linear accelerations. The processor may be configured to input the measured IMU data time histories into a machine learning model to calculate machine learning model predictions of joint positions, velocities, and accelerations. The processor may be configured to determine optimal values for the plurality of joint position design variables by optimizing the guess for the plurality of joint position design variables using a cost function, where the cost function includes a first type of error associated with matching IMU angular velocities and gravity-corrupted linear accelerations and a second type of error associated with matching joint positions, velocities, and accelerations the multibody motion data using the optimal values for the plurality of joint position design variables. The processor may be configured to generate the multibody motion data using the optimal values for the plurality of joint position design variables.

Other aspects and advantages of the claimed subject matter will be apparent from the following description and the appended claims.

DETAILED DESCRIPTION

Figure 1A:
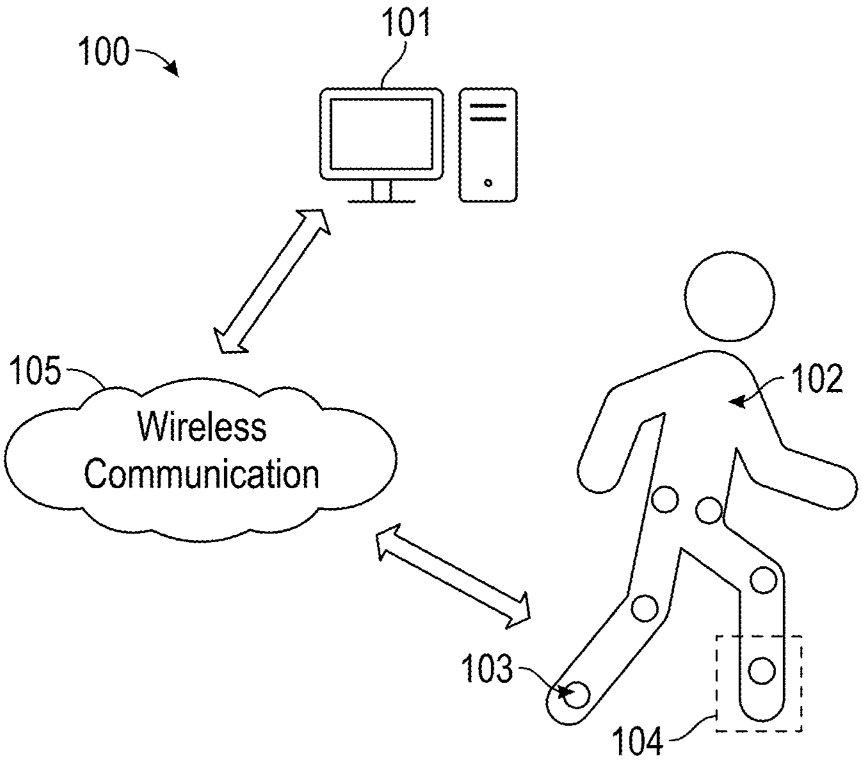
FIGS. 1A and 1B show system schematics in accordance with one or more embodiments.

Embodiments disclosed herein generally relate to a system and a method for calculating kinematic model motion data. The present method employs numerical optimization and curve fitting methods to calculate the motion of a multibody dynamic system. The present system and method provide the ability to measure the motion of a multibody system cheaply and easily in any environment and applies these concepts in a novel way to this new problem. In one or more embodiments, a system is presented that uses machine learning-informed physics models (as opposed to physics informed machine learning models) and inertial measurement units (IMUs) to measure the motion of a multibody system (e.g., the human body, a robot) in any environment (e.g., indoors with surrounding metal, outdoors, under water, in space). The system takes advantage of joint constraints in a physics-based rigid body kinematic model that approximates the structure of the real-life multibody system whose motion is being measured. In one or more embodiments, the multibody kinematic model is a standard robot-type model where individual rigid body segments are connected by constraint-based joints (e.g., pin joints, slider joints, ball-and-socket joints). The joint constraints are represented by translational (e.g., slider) and rotational (e.g., pin, ball-and-socket) joints connecting pairs of bodies in the system to each other and the base body of the system to ground. By combining physics models, machine learning models, and numerical methods, the motion measurement system can perform off-line motion measurement with greater accuracy and stability than can existing IMU-based motion measurement systems.

The method and system of one or more embodiments allows the motion of the multibody system to be measured indoors or outdoors (and even under water) with equal accuracy, and would not have limitations based on the size of the test environment, would not require a calibrated test environment, would not require special lighting or other aids within the test environment, and would be significantly less expensive, complicated, and time consuming to use compared to current methods and systems used to measure the motion of a multibody system.

Using only physics models, the calibrated system can utilize IMU data to measure the motion of joints undergoing large movements. If the system's physics models are augmented with machine learning (ML) models constructed using reference joint motion data as described in one or more embodiments herein, then the calibrated system can utilize IMU data to measure the motion of joints undergoing small movements as well. In the present system, it is desirable that one or more IMUs be placed on the base body and terminal bodies of the multibody system and that the positions and orientations of the IMUs on the body segments be known. By merging physics-based joint motion estimates with machine learning-based joint position estimates, the calibrated system produces more accurate joint motion measurements than can be achieved using physics models alone or machine learning models alone.

In contrast to existing IMU-based motion measurement systems that solve for joint motions one time frame at a time using time-marching numerical integration, the present system and method solve for joint motions over all time frames in a specified time window simultaneously without using time-marching numerical integration. Thus, the present system and method utilize experimental IMU data time histories. Herein, "experimental" denotes measured.

Embodiments disclosed herein relate to a system for generating kinematic model motion data for body segments in a multibody system. FIG. 1A shows an example system in accordance with one or more embodiments, where the multibody system is a real body. The system 100 includes at least one inertial measurement unit (IMU) 103 which is placed on a body segment 104 or body segments of the multibody system 102. The IMUs 103 transmit data wirelessly 105 to a computer system 101.

Figure 1B:
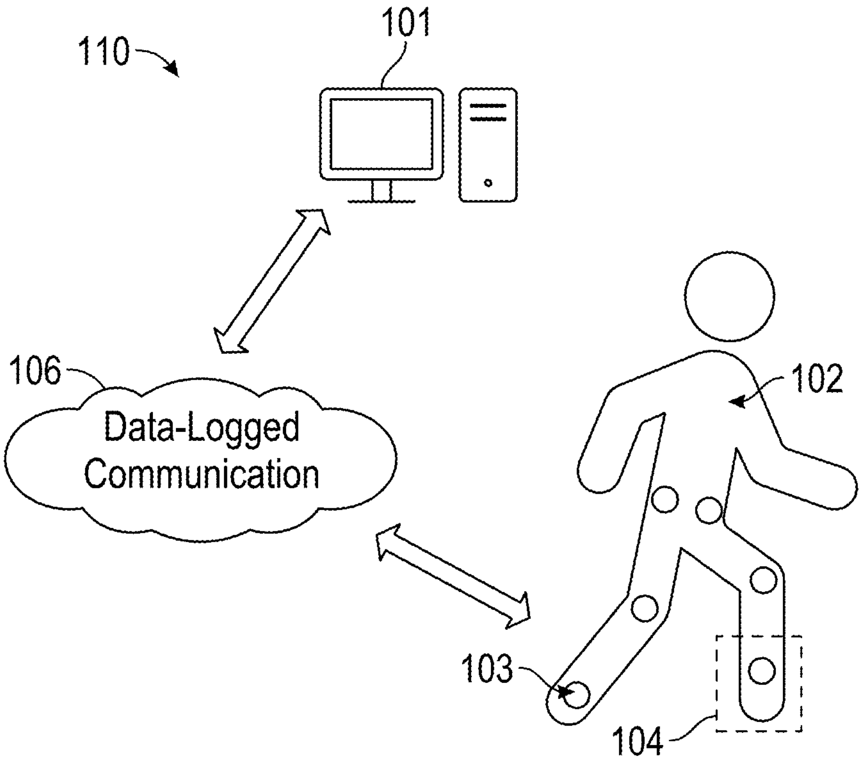

FIG. 1B shows another example system in accordance with one or more embodiments, where the multibody system is a real body. The system 110 includes at least one inertial measurement unit (IMU) 103 which is placed on a body segment 104 or body segments of the multibody system 102. The IMUs 103 transmit data without the use of a computer system 101 during the data measurement stage. The IMUs 103 are turned on in "data logging" mode. Data is collected continuously by the IMUs 103 and stored in on-board memory. After data collection is completed, data-logged communication 106 occurs, where the logged data stored in each IMU 103 is downloaded to the computer system 101.

Figure 2:
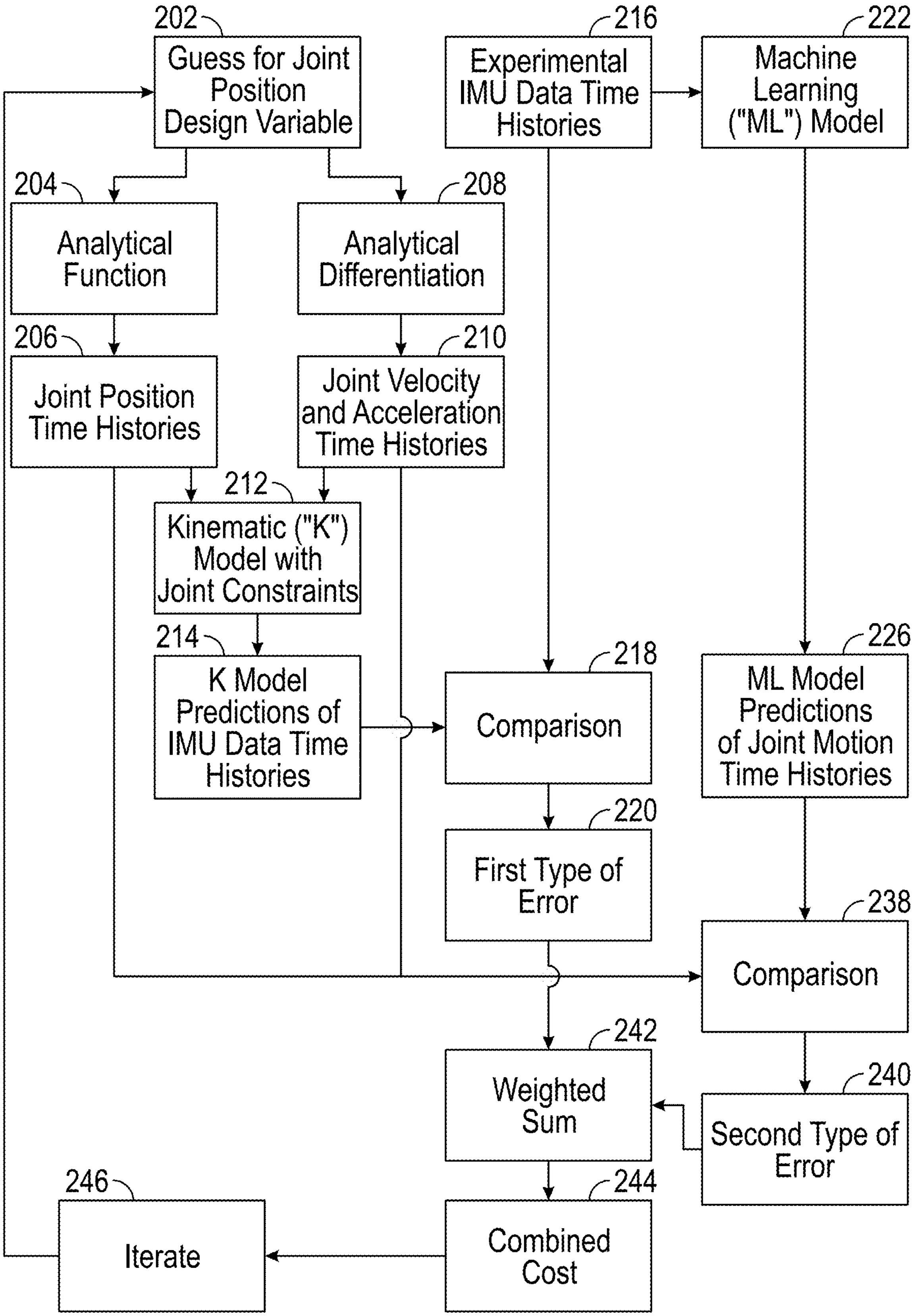
FIG. 2 shows a computational method schematic in accordance with one or more embodiments.

One or more embodiments also relate to a computer-implemented method for calculating kinematic model motion for body segments in a multibody system as depicted in the examples of FIGS. 1A and 1B. The method for calculating kinematic model motion data of one or more embodiments is represented in the flowchart of FIG. 2.

In one or more embodiments, prior to executing the method for calculating multibody motion data, the positions and orientations of the experimental IMUs 103 on the experimental (and hence also the kinematic model 212) body segments 104 are determined through a system calibration process, described further below, using experimental IMU data and an experimental method for measuring positions and/or orientations. Various known options are contemplated for performing these experimental position and/or orientation measurements. Suitable methods include (but are not limited to) optical motion capture, planar x-rays or computed tomography scans, laser scans and other three-dimensional surface scans, and stereophotogrammetry. It will be understood herein that "include" and related terms referring to inclusion are open ended so that for example "include" means include (but are not limited to)".

One or more embodiments use experimental methods to perform preliminary calibration of IMU 103 positions and orientations on the body segments 104. The calibration may include methods that do not involve the use of an optical motion capture system. Once this calibration process is performed once, the calibrated system can be used for future data collection sessions without recalibration as long as the experimental IMUs are either left on the body segments (e.g., industrial applications) or re-placed in the same positions and orientations as during calibration (e.g., human movement applications).

Similarly, calibration of machine learning models that estimate joint positions in the kinematic model from experimental IMU measurements involve reference joint motion data. Various known options are contemplated for obtaining the reference joint motion data. Suitable choices for obtaining the reference motion data include optical motion capture and markerless video motion measurement.

The proposed IMU-based motion measurement systems 100 and 110 and method utilize a novel computational algorithm, as illustrated by the schematic in FIG. 2, that combines a rigid multibody kinematic model 212, one or more machine learning models 222, curve fitting methods, and numerical optimization methods to quantify multibody system motion over a specified time window.

The ML model 222 may be constructed using any appropriate machine learning method. Suitable machine learning methods include (but not limited to) linear regression, artificial neural networks, support vector machines, and Kriging.

Given a calibrated kinematic model 212 and a guess for the model's joint position design variables, analytical functions calculate joint position time histories over a specified time window, and analytical differentiation is used to calculate joint velocity and acceleration time histories over the same time window. These time histories are input to the kinematic model 212, which uses rigid body kinematics theory to calculate estimates of the linear accelerations (including the influence of the acceleration due to gravity, henceforth called “gravity-corrupted” linear accelerations) and angular velocities of the experimental IMUs.

Notably, in the method of one or more embodiments, no calculation of IMU orientations with respect to the ground reference frame is needed to eliminate gravity corruption from the IMU linear acceleration measurements. In contrast to common approaches that use time-marching numerical integration to calculate kinematic model motion one time frame at a time, the method and system disclosed herein utilizes numerical differentiation to calculate kinematic model motion 214 over all time frames simultaneously.

Specifically, the computational algorithm illustrated in FIG. 2 uses a closed-form mathematical description of kinematic model joint positions 204 (e.g., B-splines for analytical function 202), which is then differentiated twice analytically to produce related closed-form mathematical descriptions of joint velocities and accelerations. The parameters in the closed-form mathematical model of joint positions (e.g., B-spline nodes) become the design variables in a numerical optimization, implemented through iteration 246. In this way, the design variables used to predict joint positions 206 also provide predictions of joint velocities and accelerations 210 without introducing any additional design variables, facilitating the creation of an overdetermined optimization problem. If the multibody system 100, 110 possesses a base body that rotates and translates relative to ground (e.g., as in human walking), then base body orientation about a vertical axis in the ground reference frame and translation along three mutually perpendicular axes in the ground reference frame are indeterminate but can be calculated if initial positions and velocities are known for these joints.

Given a guess for the joint position design variables 202, the numerical optimization used to determine joint motions in the kinematic model 212 uses a cost function composed of two types of errors. In one or more embodiments, the first type of error 220 is differences between model IMU 214 and experimental IMU measurements 216 of angular velocity and gravity-corrupted linear acceleration. Minimizing these differences alone produces predicted kinematic model motion that is highly accurate for rotational joints that undergo large ranges of motion during the measured movement (e.g., hip, knee, and ankle flexion during walking) but less accurate for rotational joints that undergo small ranges of motion (e.g., out-of-plane hip and ankle motions) and for translational joints. Therefore, it is advantageous to use a trained ML model 222 to improve the accuracy of the physics model 212.

Turning back to FIG. 2, the first step in the method for calculating multibody model motion data is to obtain experimental IMU measurements 216 and a guess for joint position design variables 202. Analytical functions 204 are then used to calculate joint position time histories 206. Analytical differentiation 208 is used to calculate velocity, and acceleration time histories 210 from the same set of joint position design variables 202. These time histories 206, 210 are input to the kinematic model 212 to calculate model estimates of IMU angular velocities and gravity-corrupted linear accelerations 214. Experimental IMU measurements 216 are also input to a trained machine learning (ML) model 222, where the ML model 222 predicts joint positions 226.

In FIG. 2, the guess for joint position design variables 202 may be optimized by using a cost function, which includes a first type of error 220 and a second type of error 240. The first type of error 220 arises from the difference between kinematic model IMU measurements 214 and experimental IMU measurements 216. If the first type of error 220 is large, the guess for the joint position design variables 202 is iterated systematically 246 by a numerical optimization process such that kinematic model IMU measurements 214 match experimental IMU measurements 216 as closely as possible. Once the first type of error 220 is minimized, the optimized joint position design variables are used to calculate multibody motion data, including joint position, velocity, and acceleration time histories.

Similarly, in FIG. 2, the second type of error 240 arises from differences between joint position, velocity, and acceleration time histories produced by the current guess for the joint position design variables 206 and machine learning model predictions of joint position, velocity, and acceleration time histories 226. If the second type of error 240 is large, new joint positions design variables generated by a numerical optimization process are input into the kinematic model 212 to calculate improved kinematic model joint positions.

When both types of errors, 220 and 240, are combined, a larger weight may be placed on the first type of error 220 and a smaller weight may be placed on the second type of error 240. This approach allows the ML model 222 to resolve the problem of predicting joint positions that are poorly determined by rigid body kinematics theory 212 alone due to minimal motion.

Keeping with FIG. 2, kinematic model motion data is generated by executing a combination model, where the combination model includes data from a kinematic model 212 which is informed by data generated by the machine learning model 222.

In one or more embodiments, the first type of error 220 includes a first weight factor and the second type of error 240 includes a second weight factor. The first weight factor and the second weight factor assign a relative importance to the first type of error 220 and the second type of error 240 and are combined into a weighted sum 242 in the combined cost function 244 used to optimize the combination model described above. The first type of error 220 may be weighted with a first weight W1 and the second type of error 240 may be weighted with a second weight W2 in the weighted sum 242, where the sum of the weights W1 and W2 equals one (W1+W2=1). Errors could be further reduced by tuning the weights W1, W2 in weighted sum 242 in the cost function using a two level optimization [Reinbolt, J. A., et al. (2005), J. Biomech., 38, 621-626]. In one or more embodiments, tuning these weights W1, W2 is incorporated into the method to generate kinematic model motion data. Tuning these weights W1, W2 may improve computation time.

Figure 3:
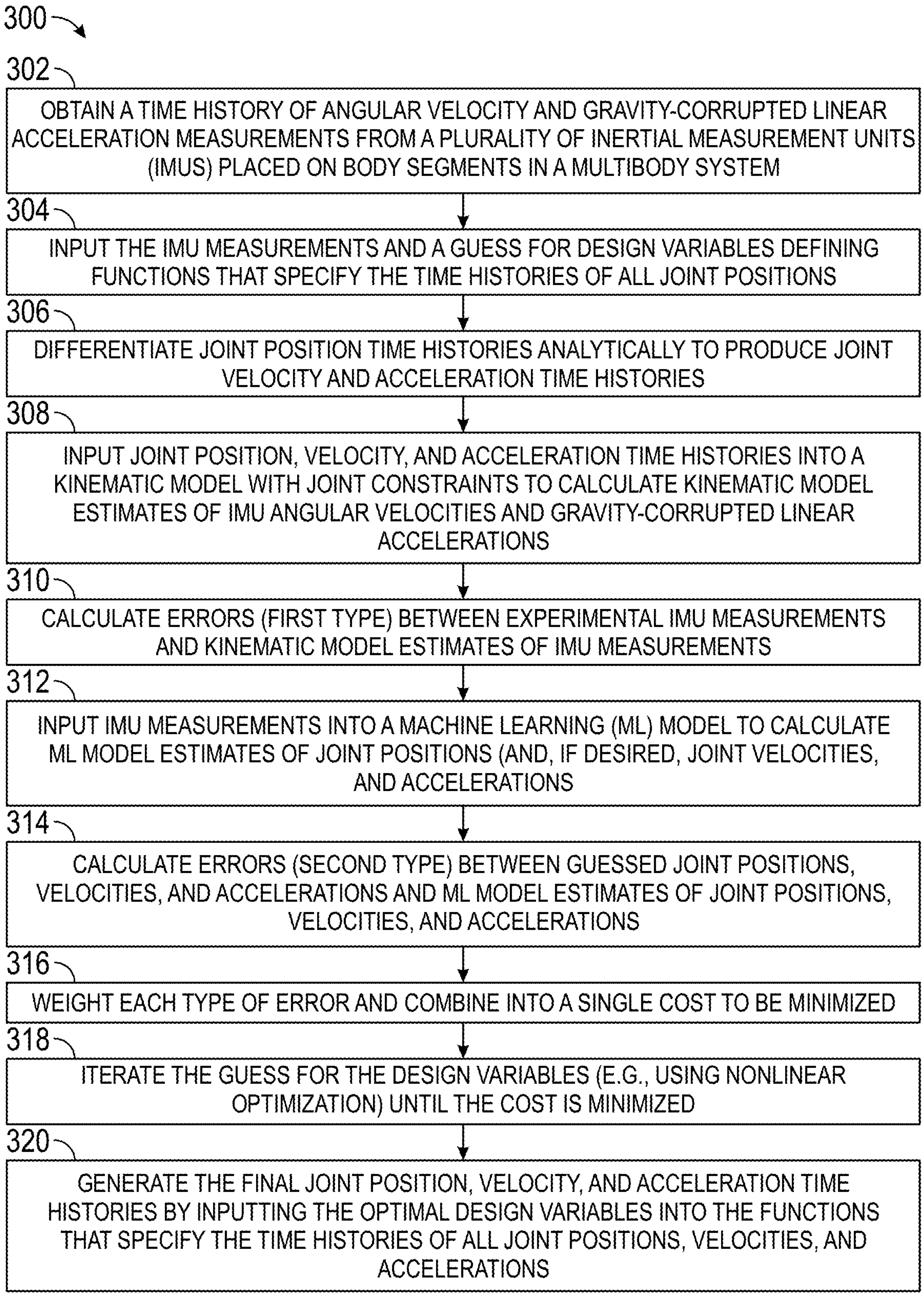
FIG. 3 shows a flowchart in accordance with one or more embodiments.

FIG. 3 depicts a flowchart in accordance with one or more embodiments disclosed herein. In block 302, a time history of angular velocity and gravity-corrupted linear acceleration measurements is obtained from a plurality of inertial measurement units (IMUs) placed on body segments in a multibody system. In some embodiments, the plurality of inertial measurement units are configured to obtain measurements. In some embodiments, a position and an orientation of each of the plurality of IMUs are calibrated prior to obtaining the measurements. In some embodiments, each experimental inertial measurement unit is calibrated using one or more of optical motion capture, planar x-rays or computed tomography scans, laser scans and other three-dimensional surface scans, and stereophotogrammetry.

Keeping with FIG. 3, in block 304 the IMU measurements and a guess for design variables defining functions that specify the time histories of all joint positions are input in an iterative computational algorithm (e.g., a numerical optimization).

Keeping with FIG. 3, in block 306 joint position time histories are differentiated analytically to produce joint velocity and acceleration time histories. Joint velocity and acceleration time histories may be used to allow the kinematic model with joint constraints to calculate estimates of IMU angular velocities and gravity-corrupted linear accelerations.

Keeping with FIG. 3, in block 308 joint position, velocity, and acceleration time histories are input into a kinematic model with joint constraints to calculate kinematic model estimates of IMU angular velocities and gravity-corrupted linear accelerations.

Keeping with FIG. 3, in block 310 errors (first type) between experimental IMU measurements and kinematic model estimates of IMU measurements are calculated.

Keeping with FIG. 3, in block 312 IMU measurements are input into a machine learning (ML) model to calculate ML model predictions of joint positions (and, if desired, joint velocities, and accelerations) time histories. In some embodiments, the machine learning model comprises a any machine learning model known to the art, including, but not limited to, linear regression models, artificial neural networks, support vector machines, Kriging models, and combinations thereof.

Keeping with FIG. 3, in block 314 errors (second type) between guessed joint positions, velocities, and accelerations and ML model estimates of joint positions, velocities, and accelerations are calculated.

Keeping with FIG. 3, in block 316 each type of error is weighted and combined into a single cost to be minimized.

Keeping with FIG. 3, in block 318 the guess for the design variables is iterated (e.g., using nonlinear optimization) until the cost is minimized. Optimal values for the plurality of joint position design variables may be determined by optimizing the guess by using a cost function, where the cost function includes the first type of error involving IMU data and, if desired, the second type of error involving joint position, velocity, and acceleration data. In some embodiments, the first type of error comprises a difference between the kinematic model IMU data and experimental IMU data. In some embodiments, the second type of error comprises a difference between the machine learning model predictions of joint position data and joint position data calculated from the current guess for the joint position design variables.

Keeping with FIG. 3, in block 320 final joint position, velocity, and acceleration time histories are generated by inputting the optimal design variables into the analytical functions that specify the time histories of all joint positions, velocities, and accelerations. In some embodiments, the multibody motion data comprises position, velocity, and acceleration time histories.

Figure 4:
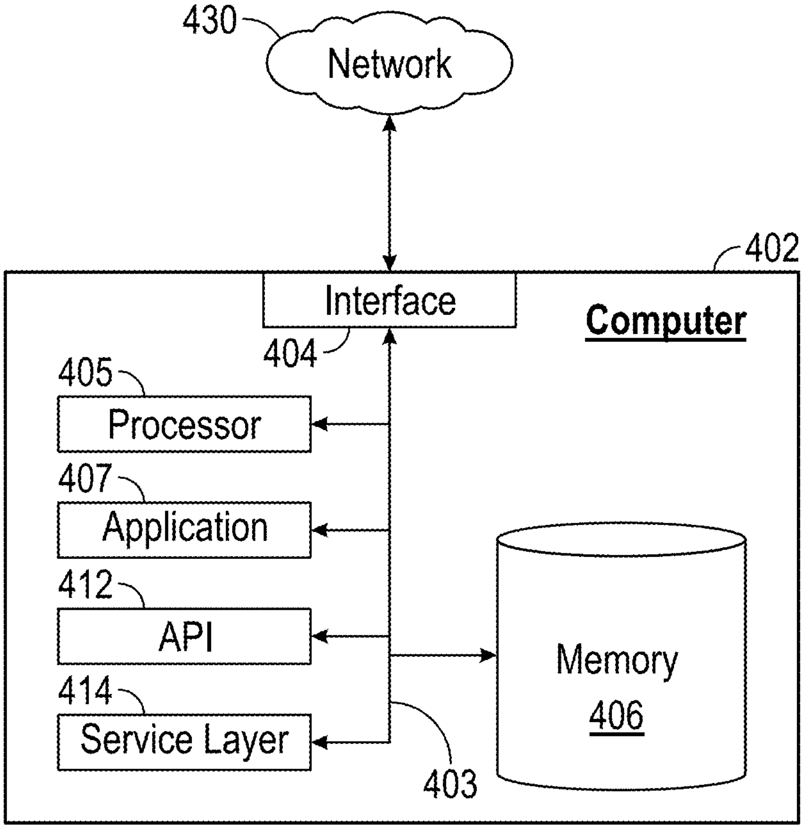
FIG. 4 shows a computer system in accordance with one or more embodiments.

FIG. 4 shows a block diagram of a computer system used to provide computational functionalities associated with described algorithms, methods, functions, processes, flows, and procedures as described in this disclosure, according to one or more embodiments. The illustrated computer 402 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 402 may include a computer that includes an input device, such as a keypad, keyboard, touch screen, or other device that can accept user information, and an output device that conveys information associated with the operation of the computer 402, including digital data, visual, or audio information (or a combination of information), or a GUI.

The computer 402 can serve in a role as a client, network component, a server, a database or other persistency, or any other component (or a combination of roles) of a computer system for performing the subject matter described in the instant disclosure. The illustrated computer 402 is communicably coupled with a network 430. In some implementations, one or more components of the computer 402 may be configured to operate within environments, including cloud-computing-based, local, global, or other environment (or a combination of environments).

At a high level, the computer 402 is an electronic computing device operable to receive, transmit, process, store, or manage data and information associated with the described subject matter. According to some implementations, the computer 402 may also include or be communicably coupled with an application server, e-mail server, web server, caching server, streaming data server, business intelligence (BI) server, or other server (or a combination of servers).

The computer 402 can receive requests over network 430 from a client application (for example, executing on another computer 402) and responding to the received requests by processing the said requests in an appropriate software application. In addition, requests may also be sent to the computer 402 from internal users (for example, from a command console or by other appropriate access method), external or third-parties, other automated applications, as well as any other appropriate entities, individuals, systems, or computers.

Each of the components of the computer 402 can communicate using a system bus 403. In some implementations, any or all of the components of the computer 402, both hardware or software (or a combination of hardware and software), may interface with each other or the interface 404 (or a combination of both) over the system bus 403 using an application programming interface (API) 412 or a service layer 413 (or a combination of the API 412 and service layer 413. The API 412 may include specifications for routines, data structures, and object classes. The API 412 may be either computer-language independent or dependent and refer to a complete interface, a single function, or even a set of APIs. The service layer 413 provides software services to the computer 402 or other components (whether or not illustrated) that are communicably coupled to the computer 402. The functionality of the computer 402 may be accessible for all service consumers using this service layer. Software services, such as those provided by the service layer 413, provide reusable, defined business functionalities through a defined interface. For example, the interface may be software written in JAVA, C++, or other suitable language providing data in extensible markup language (XML) format or another suitable format. While illustrated as an integrated component of the computer 402, alternative implementations may illustrate the API 412 or the service layer 413 as stand-alone components in relation to other components of the computer 402 or other components (whether or not illustrated) that are communicably coupled to the computer 402. Moreover, any or all parts of the API 412 or the service layer 413 may be implemented as child or sub-modules of another software module, enterprise application, or hardware module without departing from the scope of this disclosure.

The computer 402 includes an interface 404. Although illustrated as a single interface 404 in FIG. 4, two or more interfaces 404 may be used according to particular needs, desires, or particular implementations of the computer 402. The interface 404 is used by the computer 402 for communicating with other systems in a distributed environment that are connected to the network 430. Generally, the interface 404 includes logic encoded in software or hardware (or a combination of software and hardware) and operable to communicate with the network 430. More specifically, the interface 404 may include software supporting one or more communication protocols associated with communications such that the network 430 or interface's hardware is operable to communicate physical signals within and outside of the illustrated computer 402.

The computer 402 includes at least one computer processor 405. Although illustrated as a single computer processor 405 in FIG. 4, two or more processors may be used according to particular needs, desires, or particular implementations of the computer 402. Generally, the computer processor 405 executes instructions and manipulates data to perform the operations of the computer 402 and any algorithms, methods, functions, processes, flows, and procedures as described in the instant disclosure.

The computer 402 also includes a memory 406 that holds data for the computer 402 or other components (or a combination of both) that can be connected to the network 430. For example, memory 406 can be a database storing data consistent with this disclosure. Although illustrated as a single memory 406 in FIG. 4, two or more memories may be used according to particular needs, desires, or particular implementations of the computer 402 and the described functionality. While memory 406 is illustrated as an integral component of the computer 402, in alternative implementations, memory 406 can be external to the computer 402.

The application 407 is an algorithmic software engine providing functionality according to particular needs, desires, or particular implementations of the computer 402, particularly with respect to functionality described in this disclosure. For example, application 407 can serve as one or more components, modules, applications, etc. Further, although illustrated as a single application 407, the application 407 may be implemented as multiple applications 407 on the computer 402. In addition, although illustrated as integral to the computer 402, in alternative implementations, the application 407 can be external to the computer 402.

There may be any number of computers 402 associated with, or external to, a computer system containing computer 402, wherein each computer 402 communicates over network 430. Further, the term "client," "user," and other appropriate terminology may be used interchangeably as appropriate without departing from the scope of this disclosure. Moreover, this disclosure contemplates that many users may use one computer 402, or that one user may use multiple computers 402.

Possible variations to the base numerical algorithm include the following.

One or more embodiments uses a Kalman-type (e.g., extended Kalman or unscented Kalman) smoother to replace the numerical optimization process. A Kalman-type smoother can be viewed as a form of nonlinear-least squares optimization, which is an appropriate numerical optimization approach for the present IMU-based motion measurement algorithm.

One or more embodiments implement a real-time version of the computational algorithm. If IMU data are available at a high sampling frequency and kinematic model motion is calculated at a much lower sampling frequency, then the computational algorithm can be applied to time windows of the high frequency IMU data to produce joint motion estimates at the lower sampling frequency. For example, if IMU data are sampled at 1200 Hz but kinematic model motion is to be calculated at 100 Hz, then a window of 25 time frames (the current time frame plus 12 time frames before and after the current one) can be analyzed by the algorithm, which calculates kinematic model motion at the center of the time window. Because the analysis involves using IMU data at 12 future time points, the real-time joint motion calculations will possess a time lag of 0.01 seconds. Decreasing the number of future time points used by the algorithm will decrease the time lag but will also decrease motion measurement accuracy.

One or more embodiments uses a reduced set of IMUs, where IMUs are eliminated from intermediate bodies (i.e., not the base body or a terminal body) in the kinematic model structure. If one or more intermediate body IMUs are eliminated from the IMU-based motion measurement system, joint motions in the kinematic model can still be predicted with reasonable accuracy, though the accuracy will be reduced compared to the situation where at least one IMU is present on each body segment in the kinematic model.

One or more embodiments involve modifying the computational algorithm as discussed herein to make real-time motion measurement possible, though with a small amount of time delay. This time delay can be eliminated by using only past time points and the current time point to calculate kinematic model joint positions, velocities, and accelerations at all past time points and the current point simultaneously.

According to one or more embodiments, applications of the proposed system include orthopedic and rehabilitation applications. Orthopedic surgeons want to know how a patient moves prior to surgery so that this information can be used in surgical planning and following surgery so that this information can be used to assess functional outcome. Physical therapists want to know how a patient moves prior to, during, and following an intervention so that the knowledge can be used to assess patient functional improvement and to modify an intervention to facilitate greater functional improvement.

According to one or more embodiments, applications are pre-surgery motion measurement for orthopedic surgery planning, where patient motion could be measured quickly and easily in the doctor's office, and during training motion measurement for telerehabilitation evaluation, where patient rehabilitation prescriptions could be performed in a home, community, or gym setting without the assistance of a trained therapist and patient performance transmitted remotely. Another likely application is measurement of athletic performance during actual competitions as well as during training. Existing optical motion capture and IMU-based motion measurement systems cannot currently accommodate these situations.

Embodiments of the present disclosure may provide at least one of the following advantages.

1) Only IMU gyroscope and gravity-corrupted accelerometer data are involved. No IMU magnetometer data are required, eliminating problems caused by the presence of metal in the test environment.
2) No numerical integration of model state or noisy experimental IMU gyroscope or accelerometer data is required, eliminating problems caused by integration errors, integration drift, and unknown initial conditions.
3) No calculation of IMU orientations with respect to ground is required, either to determine the orientations of individual segments in the multibody system, or to remove the acceleration due to gravity from IMU accelerometer data.
4) Motion can be measured accurately for any sufficiently large block of time and for low IMU sampling frequencies (e.g., 100 Hz).
5) Joint accelerations as well as joint velocities and positions are determined simultaneously for the kinematic model, facilitating additional analyses that require joint position, velocity, and acceleration data (e.g., inverse dynamics analyses).
6) Motion can be measured when one or more IMUs are eliminated from intermediate bodies (i.e., not the base body or a terminal body), though the system produces the most accurate motion measurements when one or more IMUs are present on each body segment.

The following examples are presented to facilitate a better understanding of the embodiments disclosed herein and are in no way intended to be limiting.

EXAMPLES

Example 1

In Example 1, an example application is provided to demonstrate system performance for real-life human movement measurement. The example utilizes experimental IMU data collected from a human subject performing walking, jogging, and jumping. In addition, optical motion capture data were collected simultaneously from the same subject. The motion capture data provided the means for determining IMU positions and orientations on the body segments and for calibrating machine learning models to estimate joint positions. The calibrated system was then applied to experimental walking, jogging, and jumping IMU data not used in the calibration process. System accuracy was quantified by comparing pelvis and lower body joint motions determined using IMU data alone with corresponding joint motions calculated from optical motion capture data alone.

The present inventors have a complete working prototype of the IMU-based motion measurement system implemented and have validated the performance of the system using real-life IMU data collected from a human subject performing walking, jogging, and jumping movement trials. The system was calibrated using one motion cycle of IMU (collected at 1200 Hz) and optical motion capture (collected at 200 Hz) data taken from each of these three types of movement trials, and it was then validated by analyzing only IMU data (filtered and down sampled to 200 Hz to match motion capture data) taken from additional walking, jogging, and jumping movement trials not used in the calibration process. B-splines were used to provide closed-form mathematical relationships defining joint positions, velocities, and accelerations, where the initial guess for all B-spline nodes were set to zero to make the motion prediction problem as challenging as possible. Machine learning models were simple linear regression models. Root-mean-square errors in predicted kinematic model joint positions with respect to gold standard video motion capture measurements for the test trials are reported in the table below. Note that no knowledge of joint initial positions or velocities was used to generate these motion predictions, as no numerical integration was performed. Results are in Table 1 and FIGS. 5A-5R, 6A-6R, and 7A-7R. In FIGS. 5A-5R, 6A-6R, and 7A-7R, solid lines are inverse kinematics results calculated from optical motion capture data and dashed lines are inverse kinematic results calculated from IMU data using the method and system of one or more embodiments disclosed herein. Results in Table 1 marked with an asterisk (*) correspond to joint translations/rotations with indeterminate solutions and thus larger errors are expected for these coordinates. If initial positions and velocities were known for these coordinates, then accurate joint translations/rotations could be calculated for these coordinates as well.

Figure 5A:
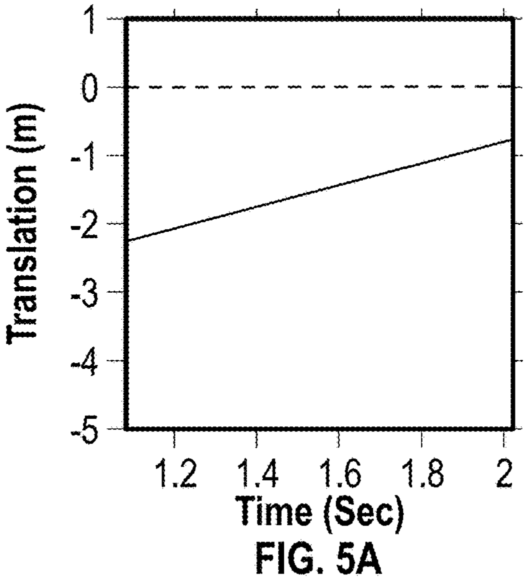
FIGS. 5A-5R show example walking data, where solid lines are inverse kinematics results from optical motion capture data and dashed lines are inverse kinematic results calculated from IMU data using the method and system in accordance with one or more embodiments.
Figure 5B:
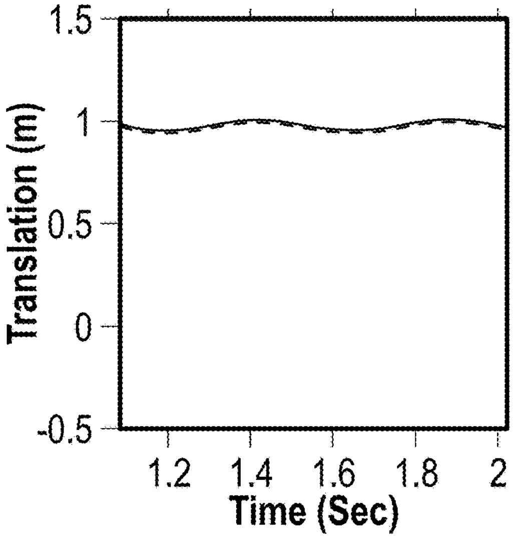
Figure 5C:
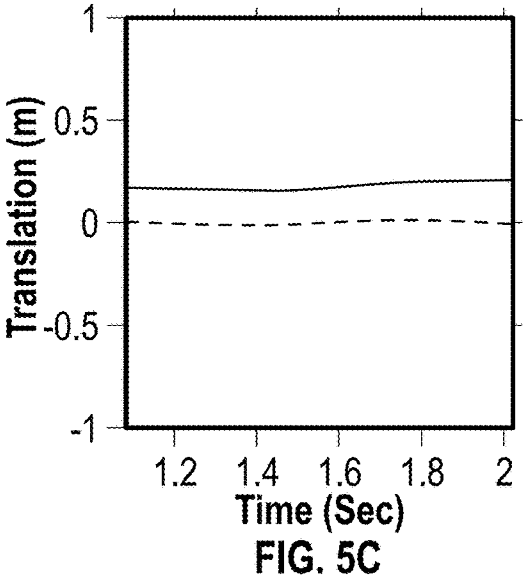
Figure 5D:
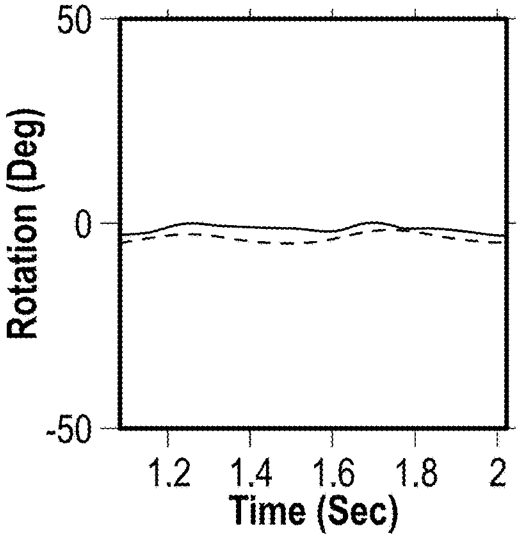
Figure 5E:
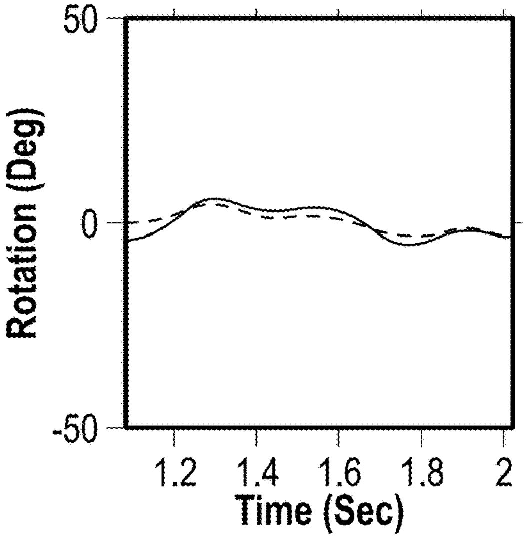
Figure 5F:
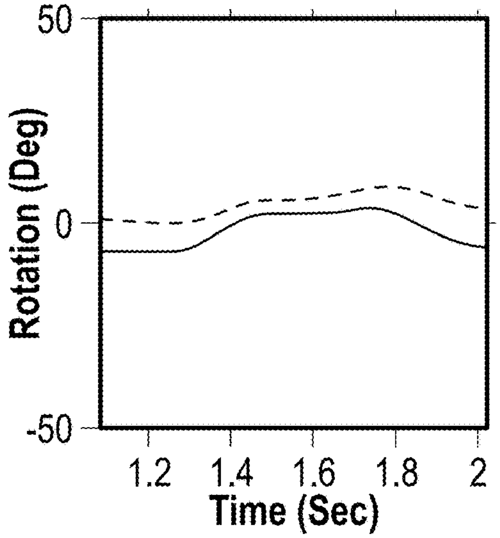
Figure 5G:
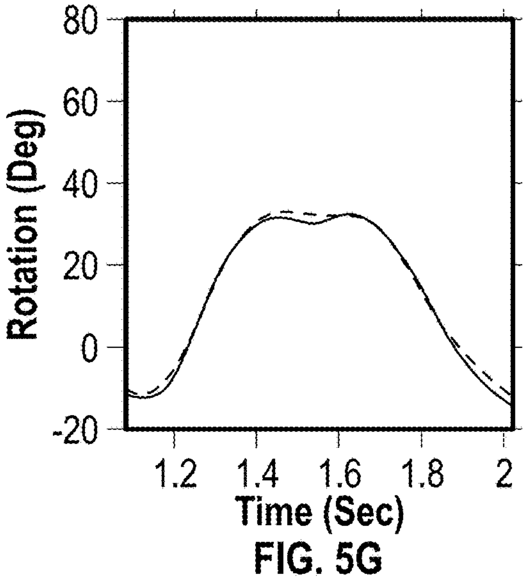
Figure 5H:
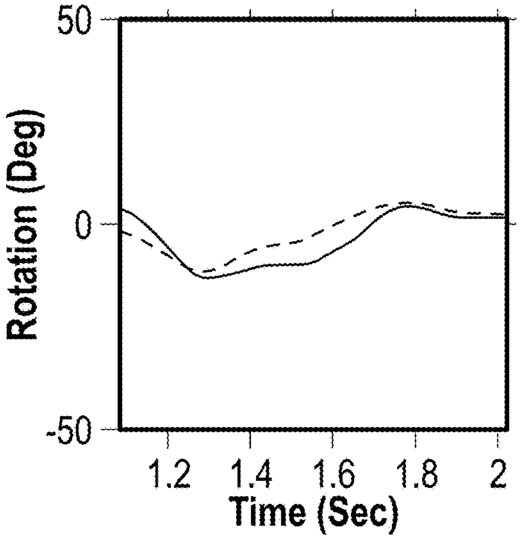
Figure 5I:
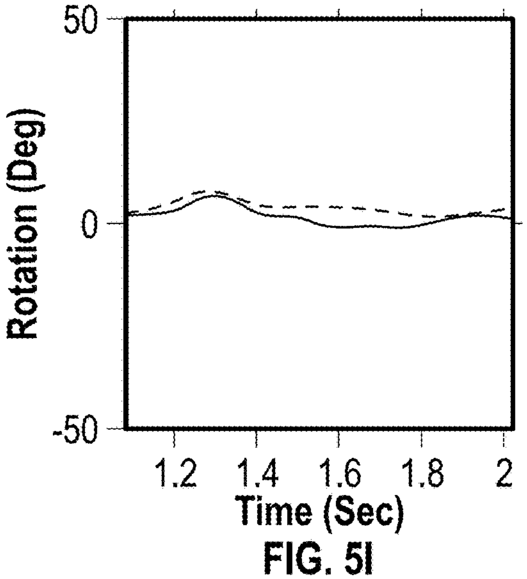
Figure 5J:
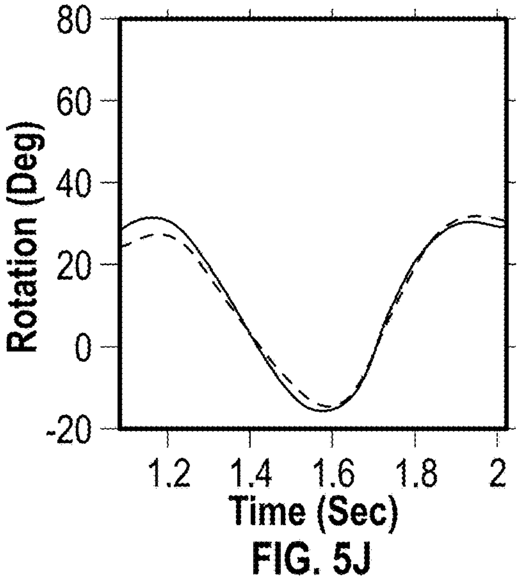
Figure 5K:
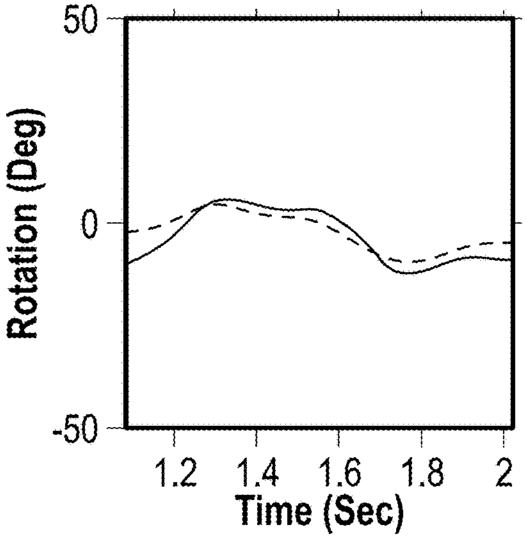
Figure 5L:
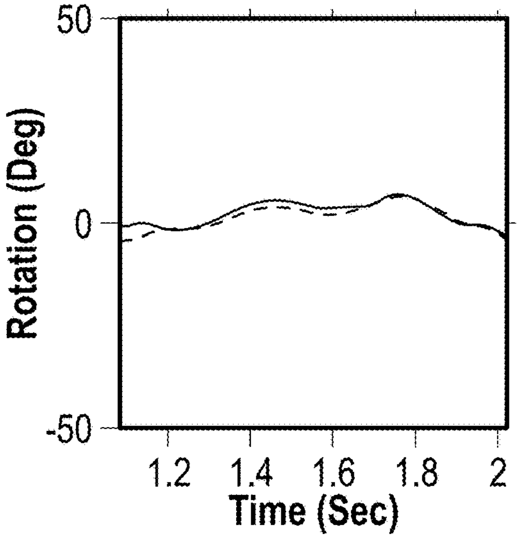
Figure 5M:
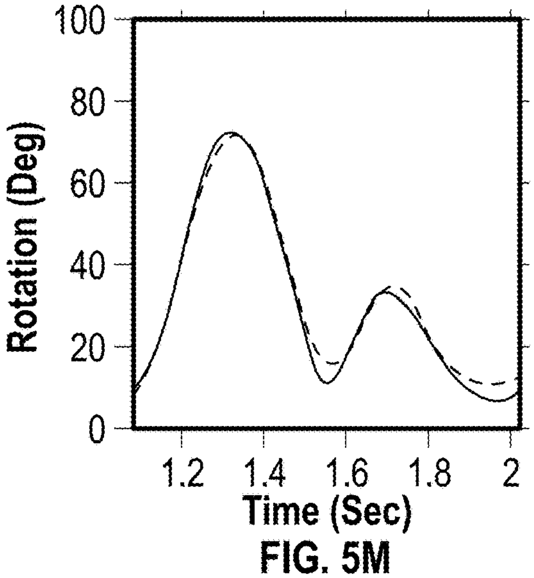
Figure 5N:
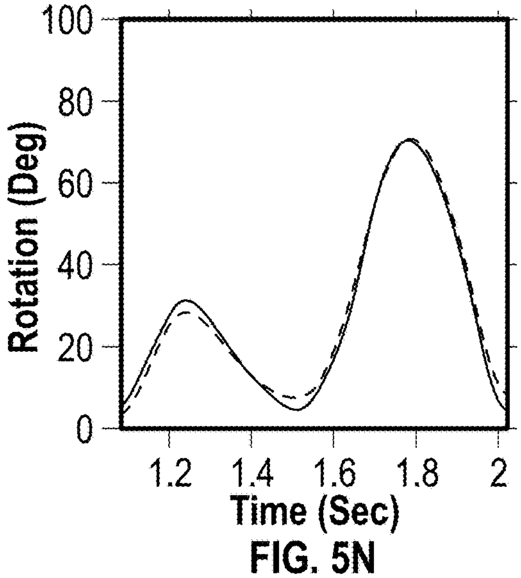
Figure 5O:
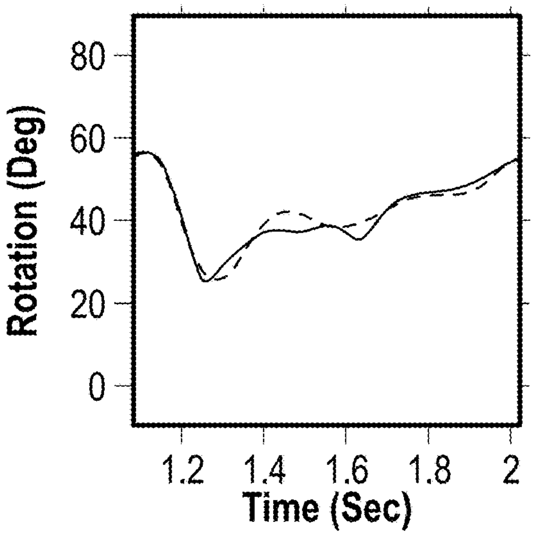
Figure 5P:
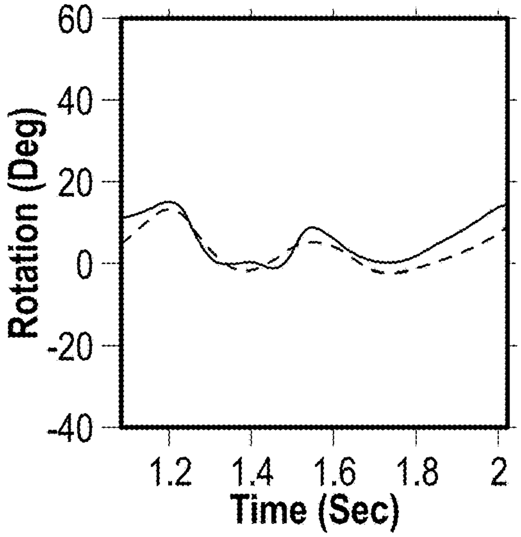
Figure 5Q:
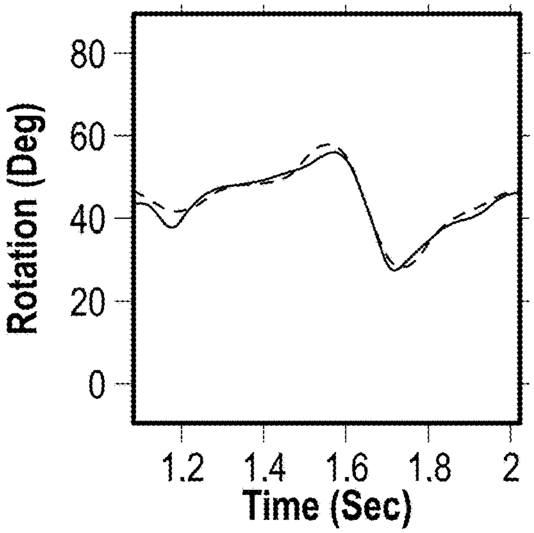
Figure 5R:
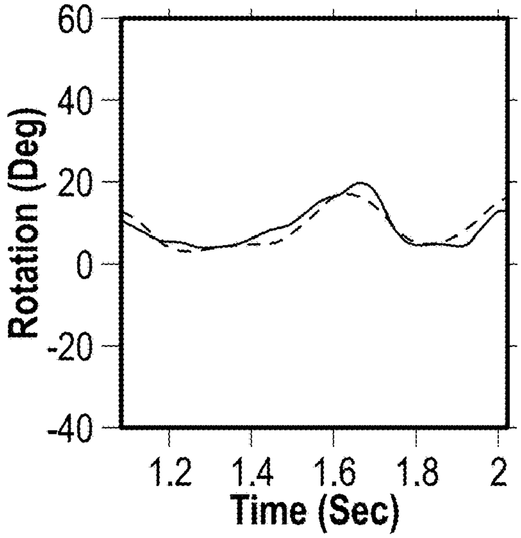

FIGS. 5A, 5B, and 5C are pelvis translations while walking. FIGS. 5D, 5E, and 5F are pelvis rotations while walking. FIGS. 5G, 5H, and 5I are right hip rotations while walking. FIGS. 5J, 5K, and 5L are left hip rotations while walking. FIGS. 5M and 5N are right and left, respectively, knee rotations while walking. FIGS. 50 and 5P are right ankle and subtalar rotations while walking. FIGS. 5Q and 5R are left ankle and subtalar rotations while walking.

Figure 6A:
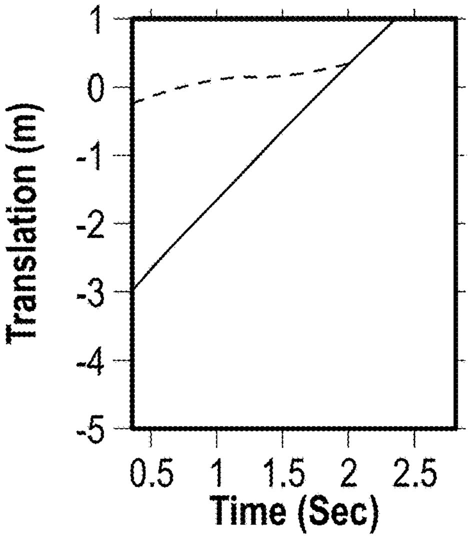
FIGS. 6A-6R show example jogging data, where solid lines are inverse kinematics results from optical motion capture data and dashed lines are inverse kinematic results calculated from IMU data using the method and system in accordance with one or more embodiments.
Figure 6B:
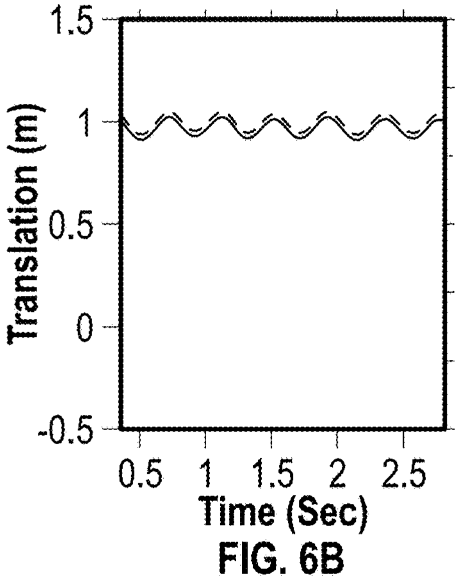
Figure 6C:
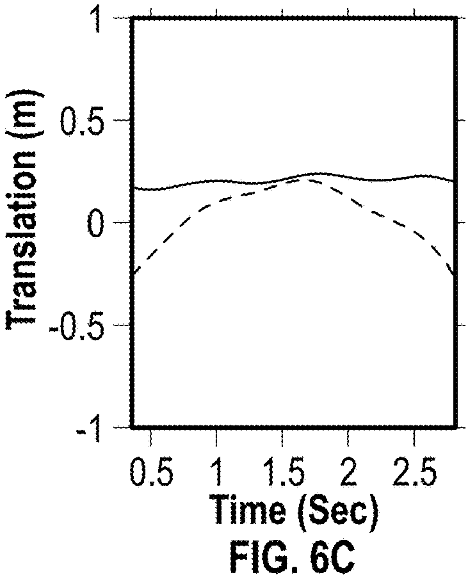
Figure 6D:
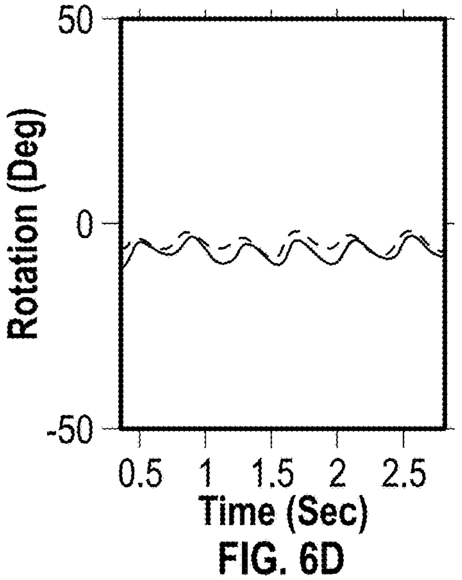
Figure 6E:
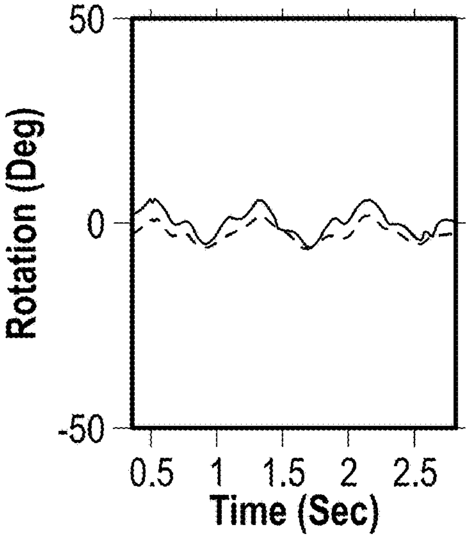
Figure 6F:
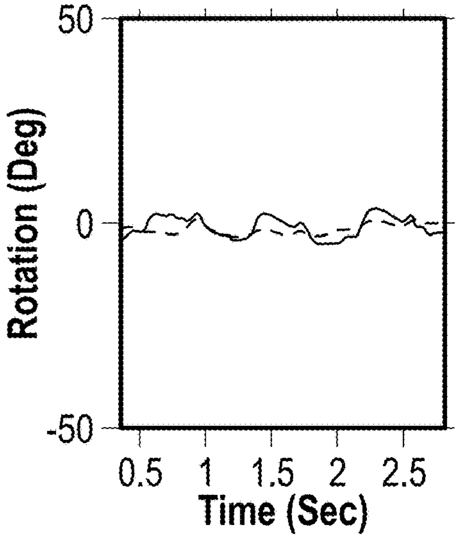
Figure 6G:
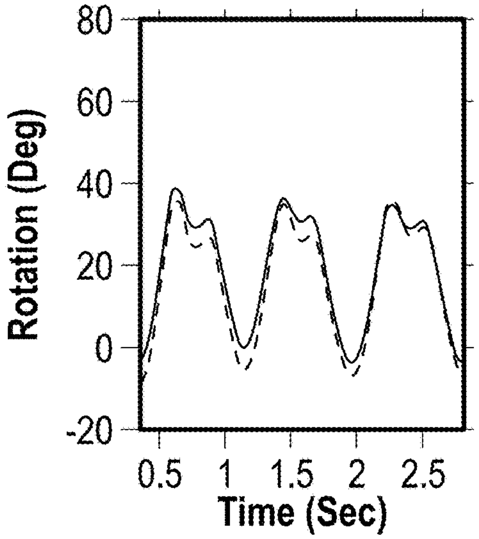
Figure 6H:
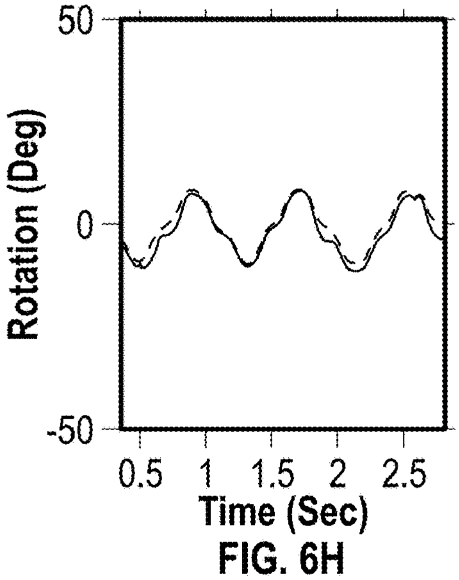
Figure 6I:
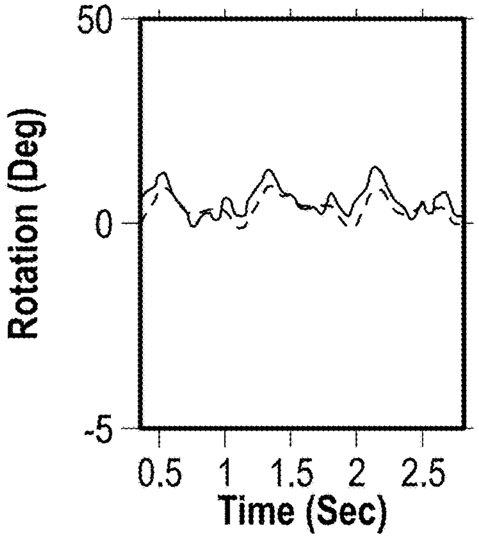
Figure 6J:
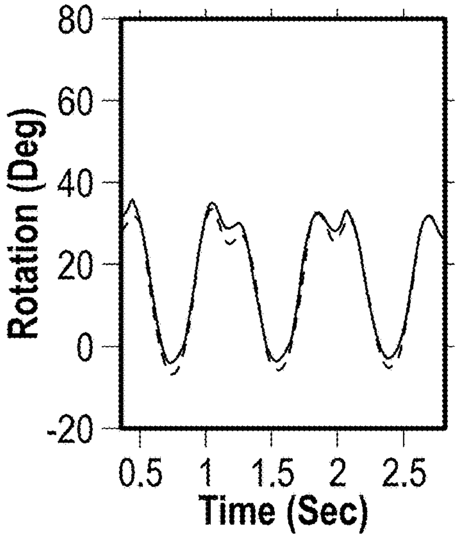
Figure 6K:
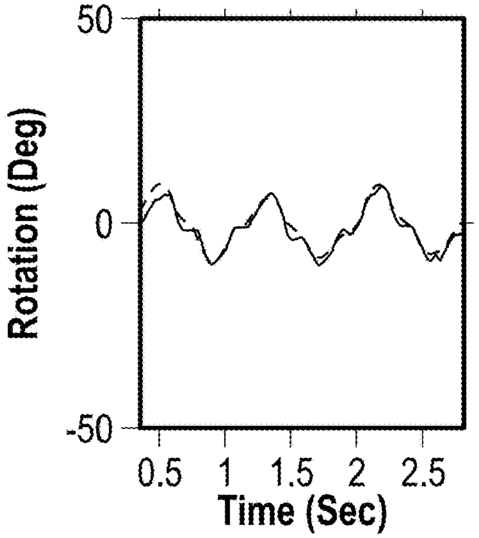
Figure 6L:
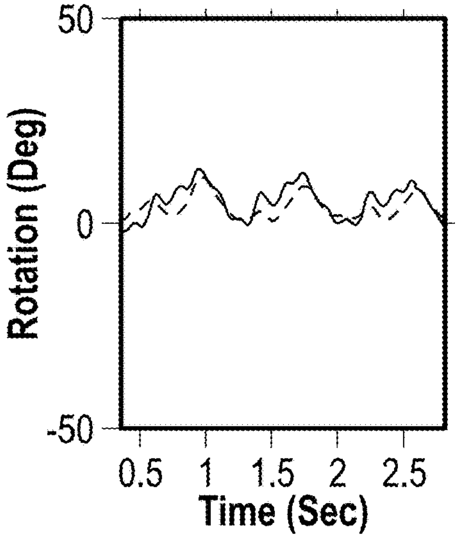
Figure 6M:
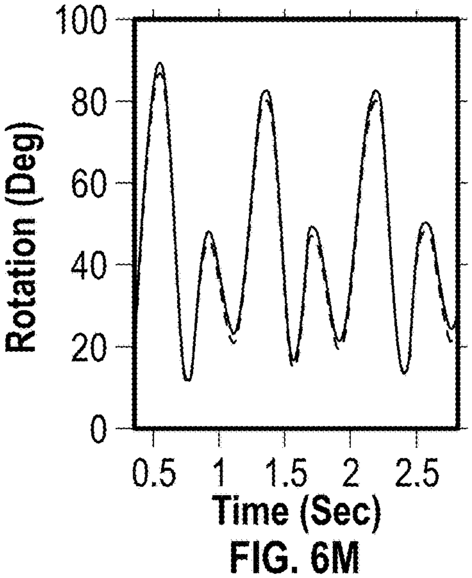
Figure 6N:
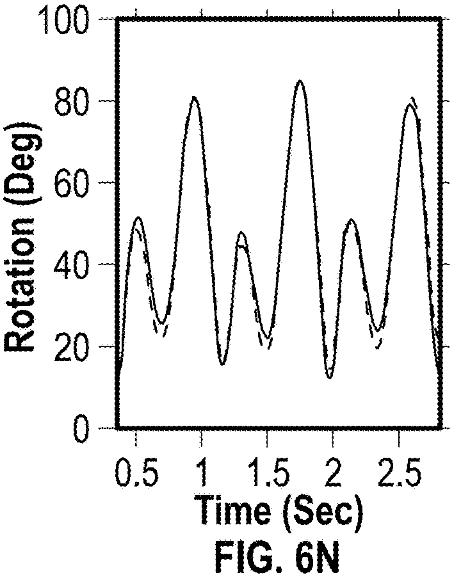
Figure 6O:
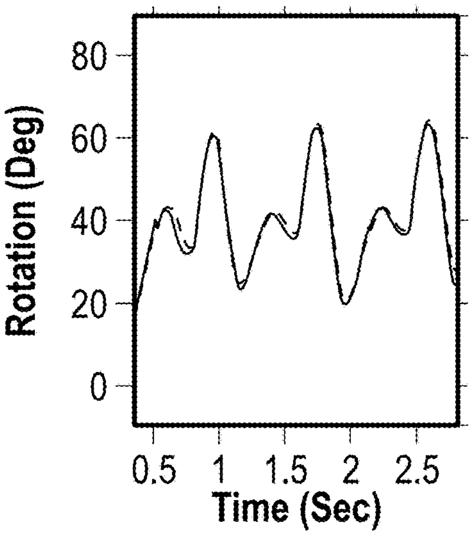
Figure 6P:
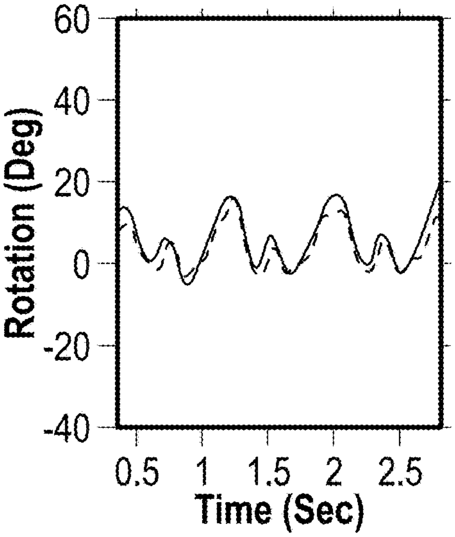
Figure 6Q:
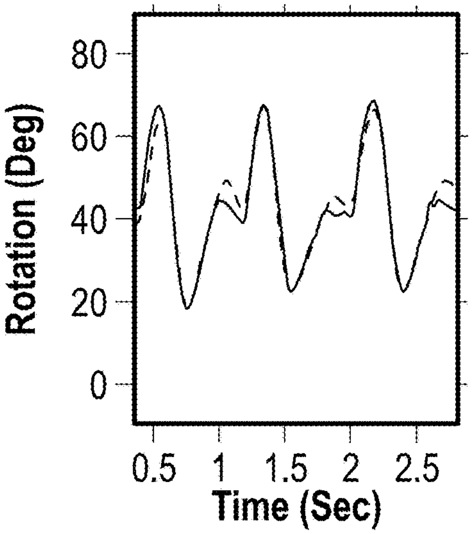
Figure 6R:
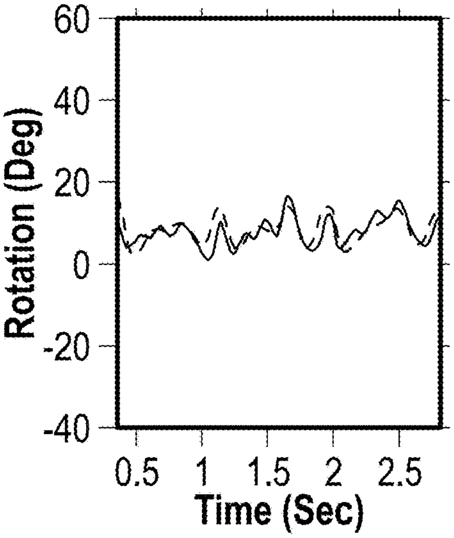

FIGS. 6A, 6B, and 6C are pelvis translations while jogging. FIGS. 6D, 6E, and 6F are pelvis rotations while jogging. FIGS. 6G, 6H, and 6I are right hip rotations while jogging. FIGS. 6J, 6K, and 6L are left hip rotations while jogging. FIGS. 6M and 6N are right and left, respectively, knee rotations while jogging. FIGS. 60 and 6P are right ankle and subtalar rotations while jogging. FIGS. 6Q and 6R are left ankle and subtalar rotations while jogging.

Figure 7A:
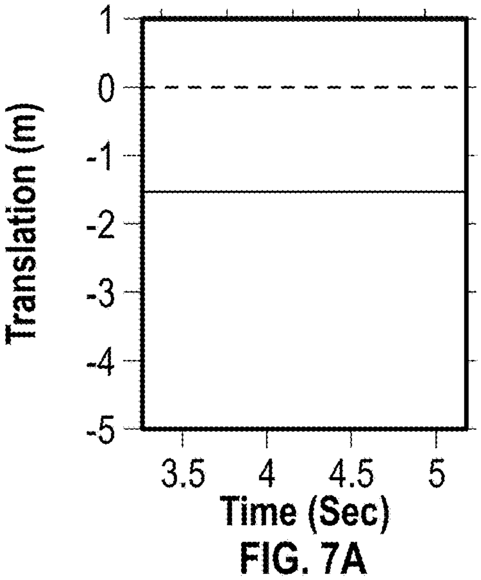
FIGS. 7A-7R show example jumping data, where solid lines are inverse kinematics results from optical motion capture data and dashed lines are inverse kinematic results calculated from IMU data using the method and system in accordance with one or more embodiments.
Figure 7B:
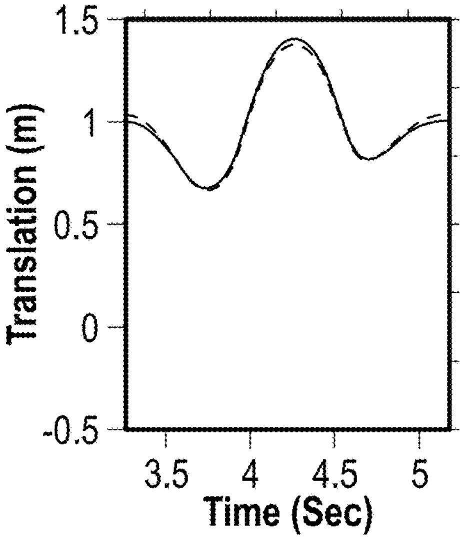
Figure 7C:
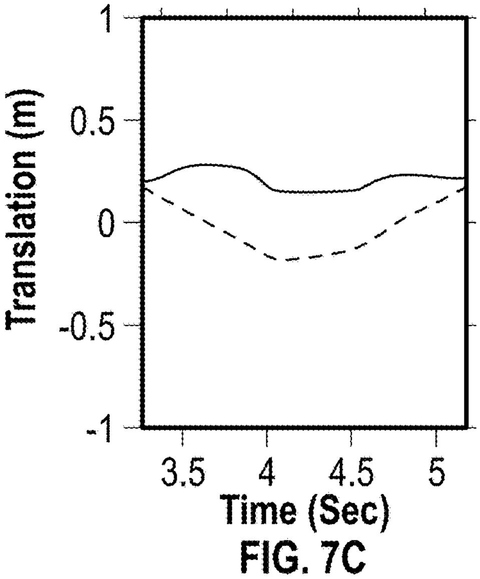
Figure 7D:
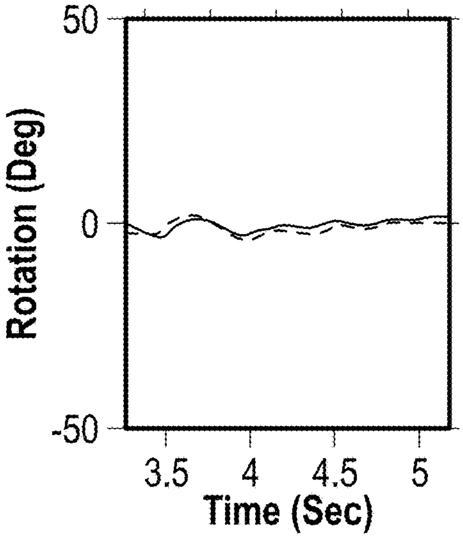
Figure 7E:
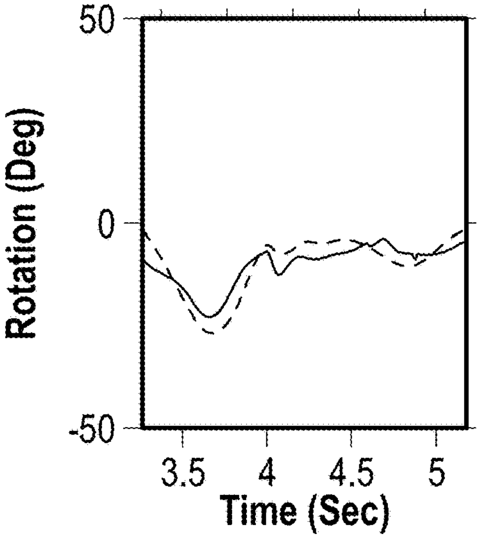
Figure 7F:
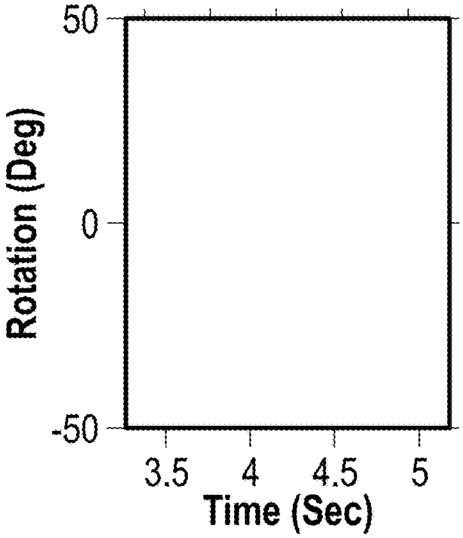
Figure 7G:
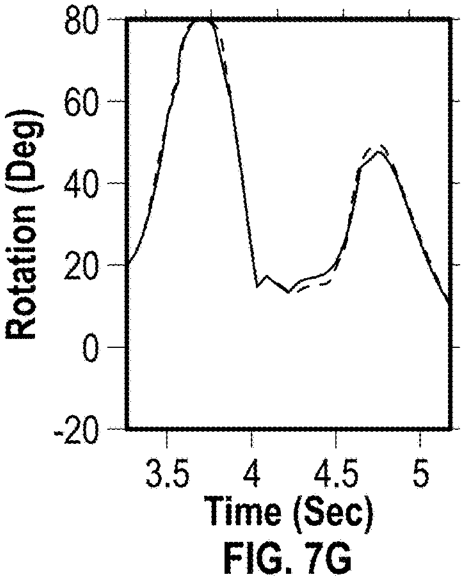
Figure 7H:
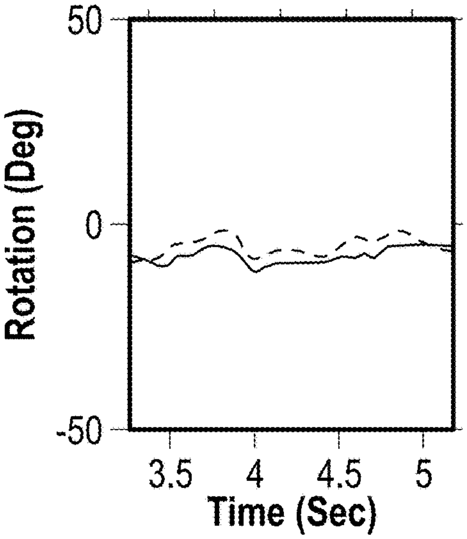
Figure 7I:
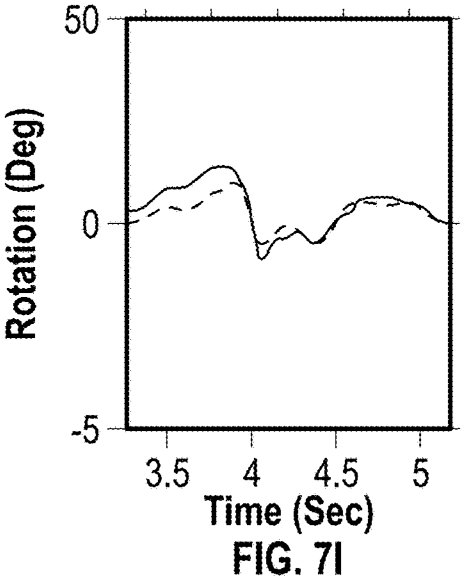
Figure 7J:
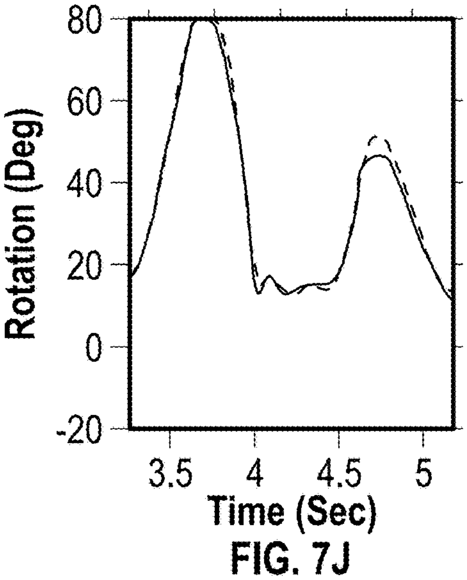
Figure 7K:
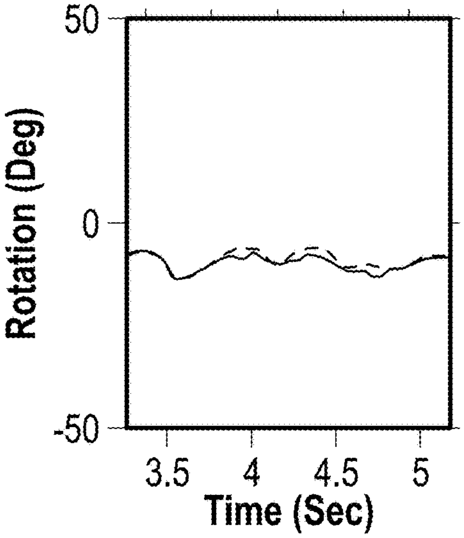
Figure 7L:
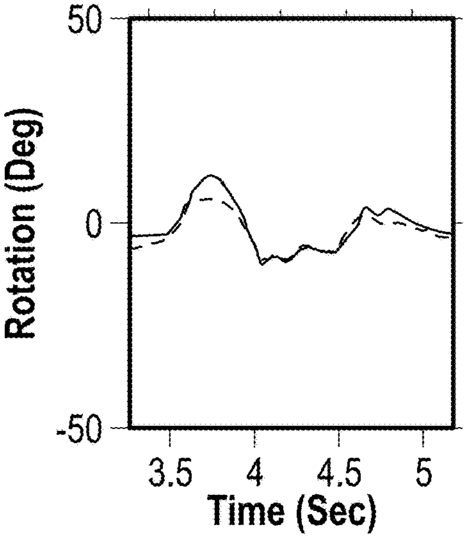
Figure 7M:
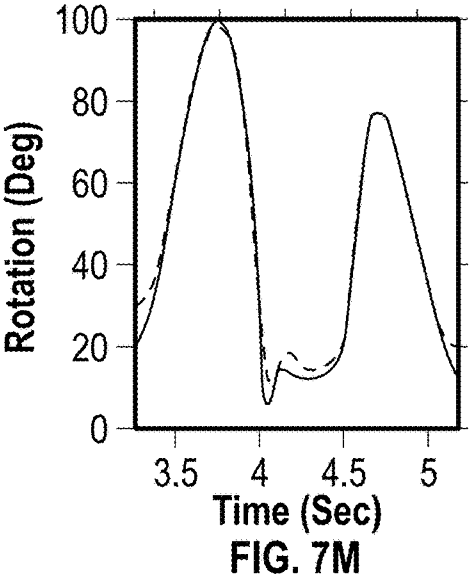
Figure 7N:
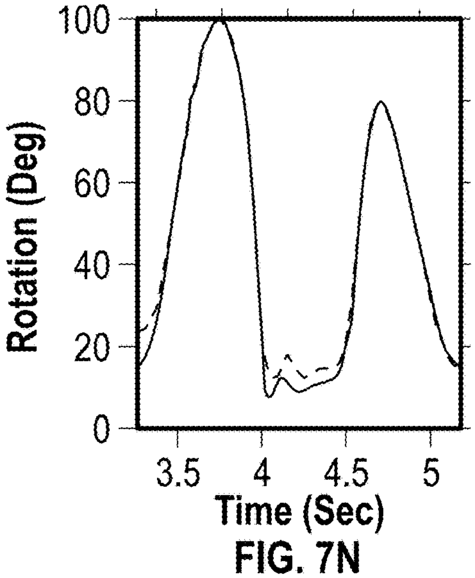
Figure 7O:
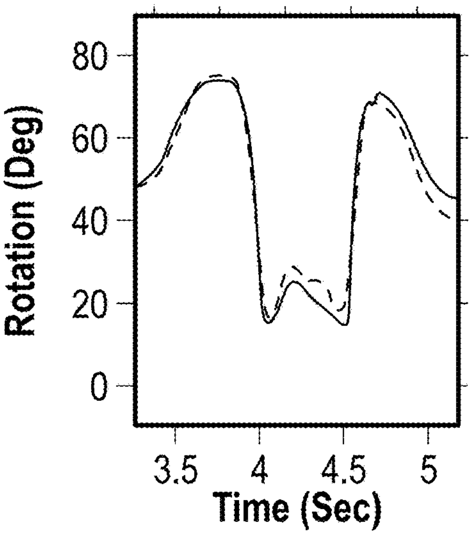
Figure 7P:
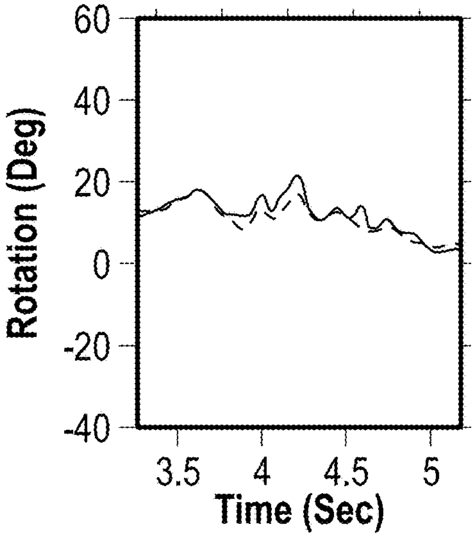
Figure 7Q:
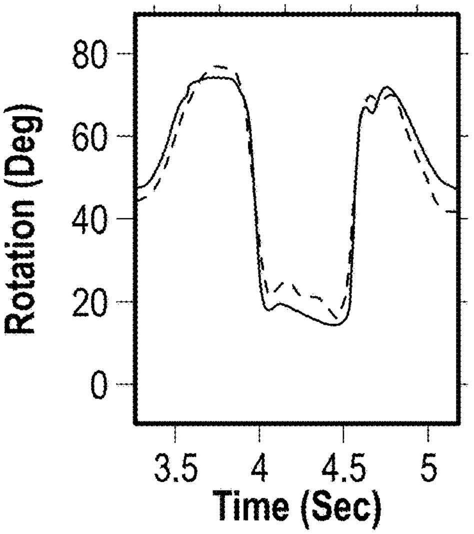
Figure 7R:
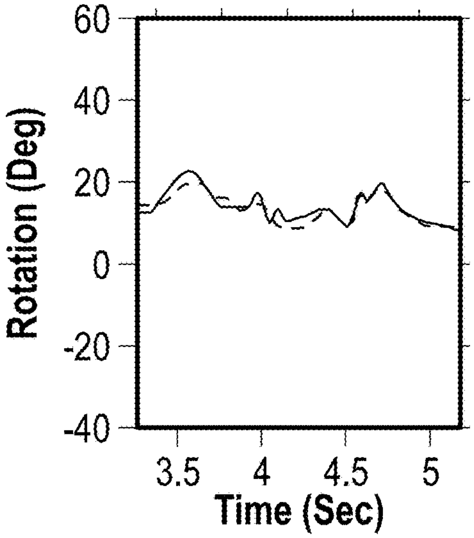

FIGS. 7A, 7B, and 7C are pelvis translations while jumping. FIGS. 7D, 7E, and 7F are pelvis rotations while jumping. FIGS. 7G, 7H, and 7I are right hip rotations while jumping. FIGS. 7J, 7K, and 7L are left hip rotations while jumping. FIGS. 7M and 7N are right and left, respectively, knee rotations while jumping. FIGS. 7O and 7P are right ankle and subtalar rotations while jumping. FIGS. 7Q and 7R are left ankle and subtalar rotations while jumping.

Table 1 provides root-mean-square error values for joint translations/rotations shown in FIGS. 5 through 7, as summarized in Table 2.

TABLE 1

| Kinematic Model Coordinate | Root-mean-square Errors Walking (3 cycles) | Jogging (2 cycles) | Jumping (1 cycle) |
|---|---|---|---|
| Pelvis forward translation (m) | 1.48 * | 1.35 * | 1.53 * |
| Pelvis vertical translation (m) | 0.01 | 0.02 | 0.03 |
| Pelvis lateral translation (m) | 0.22 * | 0.21 * | 0.32 * |
| Pelvis tilt (deg) | 2.26 | 3.56 | 1.33 |
| Pelvis list (deg) | 2.36 | 2.56 | 3.61 |
| Pelvis rotation (deg) | 4.94 | 3.48 * | 2.22 |
| Right hip flexion (deg) | 1.46 | 4.32 | 2.42 |
| Right hip adduction (deg) | 3.78 | 3.98 | 4.68 |
| Right hip rotation (deg) | 2.85 | 3.70 | 4.42 |
| Right knee flexion (deg) | 2.19 | 3.72 | 3.35 |
| Right ankle flexion (deg) | 2.31 | 3.36 | 4.65 |
| Right ankle inversion (deg) | 3.47 | 2.98 | 2.30 |
| Left hip flexion (deg) | 2.94 | 3.21 | 2.65 |
| Left hip adduction (deg) | 3.63 | 6.61 | 3.47 |
| Left hip rotation (deg) | 1.90 | 3.27 | 3.61 |
| Left knee flexion (deg) | 2.58 | 3.98 | 4.08 |
| Left ankle flexion (deg) | 1.54 | 3.96 | 4.19 |
| Left ankle inversion (deg) | 2.30 | 3.38 | 2.93 |

* Refers to results corresponding to joint translations/rotations with indeterminate solution.

TABLE 2

| Kinematic Model Coordinate | Relation between Errors in Table 1 and data presented in FIGS. 5-7. Walking (1 cycle) | Jogging (1 cycle) | Jumping (1 cycle) |
|---|---|---|---|
| Pelvis forward translation (m) | FIG. 5A | FIG. 6A | FIG. 7A |
| Pelvis vertical translation (m) | FIG. 5B | FIG. 6B | FIG. 7B |
| Pelvis lateral translation (m) | FIG. 5C | FIG. 6C | FIG. 7C |
| Pelvis tilt (deg) | FIG. 5D | FIG. 6D | FIG. 7D |
| Pelvis list (deg) | FIG. 5E | FIG. 6E | FIG. 7E |
| Pelvis rotation (deg) | FIG. 5F | FIG. 6F | FIG. 7F |
| Right hip flexion (deg) | FIG. 5G | FIG. 6G | FIG. 7G |
| Right hip adduction (deg) | FIG. 5H | FIG. 6H | FIG. 7H |
| Right hip rotation (deg) | FIG. 5I | FIG. 6I | FIG. 7I |
| Right knee flexion (deg) | FIG. 5M | FIG. 6M | FIG. 7M |
| Right ankle flexion (deg) | FIG. 5O | FIG. 6O | FIG. 7O |
| Right ankle inversion (deg) | FIG. 5P | FIG. 6P | FIG. 7P |
| Left hip flexion (deg) | FIG. 5J | FIG. 6J | FIG. 7J |
| Left hip adduction (deg) | FIG. 5K | FIG. 6K | FIG. 7K |
| Left hip rotation (deg) | FIG. 5L | FIG. 6L | FIG. 7L |
| Left knee flexion (deg) | FIG. 5N | FIG. 6N | FIG. 7N |
| Left ankle flexion (deg) | FIG. 5Q | FIG. 6Q | FIG. 7Q |
| Left ankle inversion (deg) | FIG. 5R | FIG. 6R | FIG. 7R |

Example 2

Example 2 provides another example of the present method and system. Inertial measurement units (IMUs) are an alternative to traditional optical motion capture systems that allow for data collection outside the lab and continuous monitoring for daily activities. In this study, a non-linear least squares optimization was used to convert IMU measurements into joint kinematics. The optimization calculates joint angles simultaneously over all time frames by optimizing B-spline nodes, without integrating any IMU measurements. This approach enables an accurate solution that works well with noisy experimental IMU data since integration errors are eliminated. Experimental motion capture and IMU data were collected from a single subject who performed treadmill walking at a self-selected speed. IMU data were low-pass filtered at 6 Hz using a fourth-order zero-phase-lag Butterworth filter and then downsampled to 100 Hz to match the motion capture sampling frequency. First, OpenSim model scaling [Delp S L et al. (2007). IEEE, 55:1940-50], [Seth A et al. (2018), PLOS, 14 (7): e1006223] was performed to scale a generic OpenSim model [Rajagopal A et al. (2016), IEEE, 63.10:2068-79] and attach dynamic markers and IMUs to the pelvis (6 DOFs) and lower body segments (6 DOFs per leg). Then, OpenSim inverse kinematics was performed to calculate model joint angles from the experimental motion capture data. Finally, a nonlinear least squares optimization method was implemented in MATLAB to calculate model joint kinematics over all time frames simultaneously from the noisy experimental IMU data. The cost function minimized errors between model-predicted and experimental IMU measurements by adjusting 30 B-spline nodes that defined the time history of each generalized coordinate and its first two time derivatives. Initial guesses for all nodes were set to zero.

The IMU inverse kinematics results obtained from the integration-free optimization for walking were compared with the inverse kinematics data for walking from optical motion capture of pelvis translations, pelvis rotations, hip rotations, knee rotations, ankle rotations, and subtalar rotations (not shown). The results showed similar quality to that shown in FIGS. 5A-5R. Compared to marker-based inverse kinematics results, the optimization predicted IMU-based joint positions with root-mean-square (RMS) errors of at most 2.8 deg for sagittal plane rotations and 5.7 deg for non-sagittal plane rotations. While RMS errors were large for all three pelvis translations, the estimated pelvis linear accelerations were quite reliable, suggesting that these errors could be significantly reduced if the correct pelvis initial position and velocity were known and the predicted pelvis linear accelerations were integrated.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112 (f) for any limitations of any of the claims herein, except for those in which the claim expressly uses the words 'means for' together with an associated function.

What is claimed is:

1. A computer-implemented method for calculating multibody motion data, comprising:

obtaining measured IMU data time histories with a plurality of inertial measurement units;

inputting the measured IMU data time histories and a guess for a plurality of joint position design variables into an analytical function to calculate joint position, velocity, and acceleration time histories;

inputting the calculated joint position, velocity, and acceleration time histories into a kinematic model to calculate kinematic model predictions of IMU angular velocities and gravity-corrupted linear accelerations;

inputting the measured IMU data time histories into a machine learning model to calculate machine learning model predictions of joint positions, velocities, and accelerations;

determining optimal values for the plurality of joint position design variables by optimizing the guess for the plurality of joint position design variables using a cost function, wherein the cost function comprises a first type of error associated with matching IMU angular velocities and gravity-corrupted linear accelerations and a second type of error associated with matching joint positions, velocities, and accelerations; and generating the multibody motion data using the optimal values for the plurality of joint position design variables.

2. The method of claim 1, wherein the plurality of inertial measurement units are configured to obtain the measured IMU data time histories.

3. The method of claim 1, wherein a position and an orientation of each of the plurality of inertial measurement units are calibrated prior to obtaining the measured IMU data time histories.

4. The method of claim 3, wherein the position and orientation of each inertial measurement unit on its respective body segment is calibrated using one or more of optical motion capture, planar x-rays or computed tomography scans, laser scans and other three-dimensional surface scans, and stereophotogrammetry.

5. The method of claim 1, wherein the first type of error comprises a difference between the measured IMU data time histories and the kinematic model predictions of IMU data time histories.

6. The method of claim 1, wherein the second type of error comprises a difference between analytical function and machine learning model predictions of joint position, velocity, and acceleration time histories.

7. The method of claim 1, wherein the multibody motion data comprises multibody position, velocity, and acceleration data.

8. The method of claim 1, wherein the machine learning model comprises a model selected from the group consisting of linear regression models, artificial neural networks, support vector machines, Kriging models, and combinations thereof.

9. A system for generating motion data from a multibody system, comprising:

a plurality of inertial measurement units, each configured to be placed on a corresponding segment of the multibody system; and a computer system comprising a processor configured to:

input measured IMU data time histories and a guess for a plurality of joint position design variables into an analytical function to calculate joint position, velocity, and acceleration time histories;

input the calculated joint position, velocity, and acceleration time histories into a kinematic model to calculate kinematic model predictions of IMU angular velocities and gravity-corrupted linear accelerations;

input measured IMU data time histories into a machine learning model to calculate machine learning model predictions of joint positions, velocities, and accelerations;

determine optimal values for the plurality of joint position design variables by optimizing the guess for the plurality of joint position design variables using a cost function, wherein the cost function comprises a first type of error associated with matching IMU angular velocities and gravity-corrupted linear accelerations and a second type of error associated with matching joint positions, velocities, and accelerations; and generate the motion data from a multibody system using the optimal values for the plurality of joint position design variables.

10. The system of claim 9, wherein the plurality of inertial measurement units are configured to obtain measured IMU data time histories.

11. The system of claim 9, wherein a position and an orientation of each of the plurality of inertial measurement units are calibrated prior to obtaining measured IMU data time histories.

12. The system of claim 11, wherein the position and orientation of each inertial measurement unit on its respective body segment is calibrated using one or more of optical motion capture, planar x-rays or computed tomography scans, laser scans and other three-dimensional surface scans, and stereophotogrammetry.

13. The system of claim 9, wherein the first type of error comprises a difference between measured IMU data time histories and the kinematic model predictions of IMU data time histories.

14. The system of claim 9, wherein the second type of error comprises a difference between analytical function and machine learning model predictions of joint position, velocity, and acceleration time histories.

15. The system of claim 9, wherein the motion data from a multibody system comprises multibody position, velocity, and acceleration data.

16. The system of claim 9, wherein the machine learning model comprises a model selected from the group consisting of linear regression models, artificial neural networks, support vector machines, Kriging models, and combinations thereof.

* * * * *